United States Patent
Verrier et al.

(10) Patent No.: US 10,040,055 B2
(45) Date of Patent: Aug. 7, 2018

(54) EPOXIDATION PROCESS

(71) Applicant: SCIENTIFIC DESIGN COMPANY, INC., Little Ferry, NJ (US)

(72) Inventors: Christelle Verrier, Little Ferry, NJ (US); Wojciech L. Suchanek, Wyckoff, NJ (US)

(73) Assignee: Scientific Design Company, Inc., Little Ferry, NJ (US)

( * ) Notice: Subject to any disclaimer, the term of this patent is extended or adjusted under 35 U.S.C. 154(b) by 0 days.

(21) Appl. No.: 15/579,419

(22) PCT Filed: Jun. 2, 2016

(86) PCT No.: PCT/US2016/035478
§ 371 (c)(1),
(2) Date: Dec. 4, 2017

(87) PCT Pub. No.: WO2016/196767
PCT Pub. Date: Dec. 8, 2016

(65) Prior Publication Data
US 2018/0141025 A1    May 24, 2018

Related U.S. Application Data (60) Provisional application No. 62/169,706, filed on Jun. 2, 2015, provisional application No. 62/169,766, filed on Jun. 2, 2015.

(51) Int. Cl.
*B01J 21/04*    (2006.01)
*B01J 21/08*    (2006.01)
(Continued)

(52) U.S. Cl.
CPC ........... *B01J 21/04* (2013.01); *B01J 19/0013* (2013.01); *B01J 23/04* (2013.01); *B01J 23/36* (2013.01);
(Continued)

(58) Field of Classification Search
CPC ... B01J 21/04; B01J 21/08; B01J 21/12; B01J 23/04; B01J 23/36; B01J 23/50;
(Continued)

(56) References Cited

U.S. PATENT DOCUMENTS 3,563,914 A    2/1971 Wattimena
3,702,259 A    11/1972 Nielsen
(Continued)

OTHER PUBLICATIONS

International Search Report dated Sep. 12, 2016 issued in PCT/US2016/035478.

*Primary Examiner* — Cam N. Nguyen
(74) *Attorney, Agent, or Firm* — Scully, Scott, Murphy & Presser, P.C.

(57) ABSTRACT

A method is provided for improving the performance of a silver-based epoxidation catalyst comprising a carrier. The carrier includes at least 80 percent alpha alumina and has a pore volume from 0.3 mL/g to 1.2 mL/g, a surface area from 0.3 m²/g to 3.0 m²/g, and a pore architecture that provides at least one of a tortuosity of 7 or less, a constriction of 4 or less and a permeability of 30 mdarcys or greater. A catalytic amount of silver and a promoting amount of one or more promoters is disposed on and/or in said carrier. The method further includes the steps of initiating an epoxidation reaction by reacting a feed gas composition containing ethylene and oxygen present in a ratio of from about 3.5:1 to about 12:1, in the presence of the silver-based epoxidation catalyst at a temperature of about 200° C. to about 230° C., and subsequently increasing the temperature either stepwise or continuously.

12 Claims, 1 Drawing Sheet

(51) Int. Cl.
*B01J 21/12* (2006.01)
*B01J 23/04* (2006.01)
*B01J 23/36* (2006.01)
*B01J 23/50* (2006.01)
*B01J 35/10* (2006.01)
*B01J 19/00* (2006.01)
*C07D 301/10* (2006.01)
*B01J 37/00* (2006.01)

(52) U.S. Cl.
CPC ............ *B01J 23/50* (2013.01); *B01J 35/1009* (2013.01); *B01J 35/1038* (2013.01); *B01J 35/1042* (2013.01); *B01J 35/1047* (2013.01); *B01J 37/0018* (2013.01); *C07D 301/10* (2013.01); *B01J 2219/00051* (2013.01)

(58) Field of Classification Search
CPC ............ B01J 35/1009; B01J 35/1038; B01J 35/1042; B01J 35/1047; B01J 19/0013; C07D 301/10
See application file for complete search history.

(56) References Cited

U.S. PATENT DOCUMENTS

| | | | | |
|---|---|---|---|---|
| 4,410,453 | A * | 10/1983 | Kiovsky | B01J 23/50 502/253 |
| 4,419,276 | A | 12/1983 | Bhasin et al. | |
| 4,761,394 | A | 8/1988 | Lauritzen | |
| 4,766,105 | A | 8/1988 | Lauritzen | |
| 4,874,879 | A | 10/1989 | Lauritzen et al. | |
| 4,908,343 | A | 3/1990 | Bhasin | |
| 5,011,807 | A | 4/1991 | Hayden et al. | |
| 5,057,481 | A | 10/1991 | Bhasin | |
| 5,099,041 | A | 3/1992 | Hayden et al. | |
| 5,102,848 | A | 4/1992 | Soo et al. | |
| 5,112,795 | A | 5/1992 | Minahan et al. | |
| 5,155,242 | A | 10/1992 | Shankar et al. | |
| 5,187,140 | A | 2/1993 | Thorsteinson et al. | |
| 5,380,885 | A * | 1/1995 | Kemp | B01J 23/688 502/315 |
| 5,407,888 | A | 4/1995 | Herzog et al. | |
| 5,597,773 | A * | 1/1997 | Evans | B01J 23/688 502/308 |
| 5,663,385 | A * | 9/1997 | Kemp | B01J 23/688 502/347 |
| 5,703,253 | A * | 12/1997 | Evans | B01J 23/688 502/308 |
| 5,801,259 | A | 9/1998 | Kowaleski | |
| 6,562,749 | B1 | 5/2003 | Lednor et al. | |
| 7,102,022 | B2 | 9/2006 | Evans et al. | |
| 7,439,375 | B2 * | 10/2008 | Lockemeyer | B01J 21/04 549/534 |
| 7,485,597 | B2 | 2/2009 | Lockemeyer et al. | |
| 7,560,577 | B2 * | 7/2009 | Hirota | B01J 23/50 502/117 |
| 7,714,152 | B2 * | 5/2010 | Pak | B01J 23/50 423/628 |
| 8,008,515 | B2 * | 8/2011 | Shima | B01J 23/66 502/243 |
| 8,017,546 | B2 * | 9/2011 | Shima | B01J 23/50 502/243 |
| 8,084,390 | B2 * | 12/2011 | Gerdes | B01J 23/50 502/347 |
| 8,357,813 | B2 * | 1/2013 | Gerdes | B01J 23/50 502/347 |
| 8,456,294 | B2 * | 6/2013 | Emigh | B60R 25/1004 340/425.5 |
| 8,685,883 | B2 * | 4/2014 | Bryden | B01J 21/04 423/600 |
| 8,716,504 | B2 * | 5/2014 | Liu | B01J 21/04 502/241 |
| 8,871,677 | B2 * | 10/2014 | Richard | C07C 213/04 502/347 |
| 8,987,483 | B2 * | 3/2015 | Basrur | C07D 301/10 549/536 |
| 9,073,035 | B2 * | 7/2015 | Richard | C07D 301/10 |
| 9,339,798 | B2 * | 5/2016 | Richard | C07D 301/10 |
| 2009/0082584 | A1 | 3/2009 | Rizkalla et al. | |
| 2010/0056816 | A1 * | 3/2010 | Wallin | B01D 67/0041 549/534 |
| 2010/0267973 | A1 | 10/2010 | Liu et al. | |
| 2012/0022277 | A1 * | 1/2012 | Hashimoto | B01J 23/002 549/534 |
| 2013/0231493 | A1 * | 9/2013 | Shishkov | C07D 301/10 549/513 |
| 2014/0100379 | A1 | 4/2014 | Richard et al. | |
| 2014/0187807 | A1 | 7/2014 | Pak | |
| 2015/0209774 | A1 * | 7/2015 | Richard | C07C 213/04 502/347 |
| 2018/0021755 | A1 * | 1/2018 | Suchanek | B01J 23/50 |

* cited by examiner

EPOXIDATION PROCESS

CROSS REFERENCE TO RELATED APPLICATIONS

The present invention claims the benefit of U.S. Provisional Patent Application Nos. 62/169,706 and 62/169,766 filed Jun. 2, 2015, the entire content and disclosure of each are incorporated herein by reference.

FIELD OF THE INVENTION

The present invention relates to a method for operating a silver-based epoxidation catalyst.

BACKGROUND

Though present in natural settings at minute quantities, ethylene oxide was first synthesized in a laboratory setting in 1859 by French chemist Charles-Adolphe Wurtz using the so-called "chlorohydrin" process. However, the usefulness of ethylene oxide as an industrial chemical was not fully understood in Wurtz's time; and so industrial production of ethylene oxide using the chlorohydrin process did not begin until the eve of the First World War due at least in part to the rapid increase in demand for ethylene glycol (of which ethylene oxide is an intermediate) as an antifreeze for use in the rapidly growing automobile market. Even then, the chlorohydrin process produced ethylene oxide in relatively small quantities and was highly uneconomical.

The chlorohydrin process was eventually supplanted by another process, the direct catalytic oxidation of ethylene with oxygen, the result of a second breakthrough in ethylene oxide synthesis, discovered in 1931 by another French chemist Theodore Lefort. Lefort used a solid silver catalyst with a gas phase feed that included ethylene and utilized air as a source of oxygen.

In the eighty years since the development of the direct oxidation method, the production of ethylene oxide has increased so significantly that today it is one of the largest volume products of the chemicals industry, accounting, by some estimates, for as much as half of the total value of organic chemicals produced by heterogeneous oxidation. Worldwide production in the year 2010 was about 22 million tons. About seventy percent of the ethylene oxide produced is further processed into ethylene glycol; about twenty percent of manufactured ethylene oxide is converted to other ethylene oxide derivatives and only a relatively small amount of ethylene oxide is used directly in applications such as vapor sterilization.

The growth in the production of ethylene oxide has been accompanied by continued intensive research on ethylene oxide catalysis and processing, which remains a subject of fascination for researchers in both industry and academia. Of particular interest in recent years has been the proper operating and processing parameters for the production of ethylene oxide using so-called "high selectivity catalysts", that is Ag-based epoxidation catalysts that contain small amounts of "promoting" elements such as rhenium and cesium.

With respect to these Re-containing catalysts, there has been considerable interest in determining the optimum conditioning or start-up conditions, since Re-containing catalysts require a conditioning period to maximize selectivity.

These conditioning procedures are often directed to regulating the reactor feed during conditioning, in particular by ensuring the catalyst has a performance-enhancing amount of chloride. The presence of chloride in the reactor feed plays a key role in maintaining the catalyst's selectivity—the efficiency of the partial oxidation of ethylene to ethylene oxide. This is especially the case with respect to rhenium-containing catalysts, which are very dependent on the presence of chlorides to achieve optimal performance Examples of such procedures were previously disclosed in U.S. Pat. No. 4,874,879 to Lauritzen et al. and U.S. Pat. No. 5,155,242 to Shanker et al., which disclose start-up processes in which a Re-containing catalyst is pre-chlorinated prior to the introduction of oxygen into the feed and the catalyst is allowed to "pre-soak" in the presence of the chloride at a temperature below that of the operating temperature. While some improvement in overall catalyst performance has been reported using these prior art methods, the pre-soaking and conditioning nonetheless impose a substantial delay before normal ethylene oxide production can begin after oxygen is added into the feed. This delay in production may either partially or entirely negate the benefit of increased selectivity performance of the catalyst.

With respect to other components of the reactor feed, being conditioned in an environment that has a relatively low ethylene to oxygen ratio can also affect the performance of the catalyst. Typically Re-containing catalysts make use of relatively low ratios of ethylene to oxygen in the reactor feed to achieve maximum catalyst performance. Additionally, other patents increase the carbon dioxide in the feed to allow the reaction temperature to be increased to sufficiently to initiate or condition the catalyst while also suppressing the ethylene conversion in the reactor. An example of this procedure can be seen in U.S. Pat. No. 4,766,105 to Lauritzen, where carbon dioxide concentrations are as high as 7 mol % during the start-up.

Temperature is also an important aspect of conditioning—as shown, for example, in the proposed start-up process disclosed in U.S. Pat. No. 7,102,022 to Evans et al., which discloses contacting a Re-containing catalyst bed with a feed comprising oxygen and holding the temperature of the catalyst bed above 260° C. for a period of time of up to 150 hours. A similar technique is disclosed in U.S. Pat. No. 7,485,597 to Evans et al., but in this case the catalyst bed is held above 250° C. In both cases, after conditioning is completed and a peak selectivity value obtained, the temperature is lowered until the desired level of productivity is reached.

Again, while some improvement in catalyst performance may be obtained by this prior art method, there are also inherent disadvantages to this process. In particular, while these high-temperature conditioning processes may be necessary for activating the catalyst to obtain peak selectivity, such higher temperatures can also detrimentally modify the surface characteristics of the catalyst thus, reducing the selectivity as well as the activity of the catalyst, the latter of which forces the operator to increase temperature in order to maintain the desired level of production. The detrimental effects of high temperature conditioning may be particularly pronounced in the case of highly active Re-containing catalysts.

For these reasons there is a continuing need in the art for conditioning procedures for use in olefin epoxidation that do not detrimentally affect the performance of catalysts.

SUMMARY

A method is provided for improving the performance of a silver-based epoxidation catalyst comprising a carrier. The carrier includes at least 80 percent alpha alumina and has a pore volume from 0.3 mL/g to 1.2 mL/g, a surface area from 0.3 m²/g to 3.0 m²/g, and a pore architecture that provides at least one of a tortuosity of 7 or less, a constriction of 4 or less and a permeability of 30 mdarcys or greater. A catalytic amount of silver and a promoting amount of one or more promoters is disposed on and/or in said carrier. The method further includes the steps of initiating an epoxidation reaction by reacting a feed gas composition containing ethylene and oxygen present in a ratio of from about 2.5:1 to about 12:1, in the presence of the silver-based epoxidation catalyst at a temperature of about 200° C. to about 230° C., and subsequently increasing the temperature either stepwise or continuously.

DETAILED DESCRIPTION

The present invention will now be described in greater detail by referring to the following discussion and drawings that accompany the present invention. In the following description, numerous specific details are set forth, such as particular structures, components, materials, dimensions, processing steps and techniques, in order to provide an understanding of the various embodiments of the present invention. However, it will be appreciated by one of ordinary skill in the art that the various embodiments of the present invention may be practiced without these specific details. As used throughout the present invention, the term "about" generally indicates no more than ±10%, ±5%, ±2%, ±1% or ±0.5% from a number.

The present invention is directed to an epoxidation process for use with catalysts that, when prepared upon carriers characterized by the pore architectures described in the present application, are particularly active and thus susceptible to surface modification, particularly in environments of relatively low ethylene to oxygen ratios. The present invention will describe these carriers and their characterizing pore architecture in more detail, then describe the catalysts made upon them that are particularly active and highly susceptible to surface modification, and then describe the inventive epoxidation process, which includes primarily an epoxidation initiation process.

It has been discovered in the present invention that catalysts made upon carriers with the characterizing pore architecture described below are highly active and subject to surface modification, particularly when initiated at high temperatures in a gaseous environment having a relatively low ethylene to oxygen ratio. Thus, superior performance can be obtained by avoiding such surface modification during the initiation process, in particular by conditioning at lower temperatures and especially by avoiding such environments. Moreover, it has been further discovered that such catalysts can be initiated without the necessity of adding high concentrations of CO2 to suppress ethylene conversation—providing the additional advantage that a plant operator may immediately begin to produce appreciable amounts of ethylene oxide during initiation.

Typical representations of porous body microstructures, e.g., catalyst carriers for epoxidation of olefins, include the following measurable features and variety of their combinations: (1) Pore size distribution represented either as cumulative intrusion curves or as log differential size distributions, (2) Ranges of pore sizes with assigned specific pore volumes or pore volume fractions of total materials pore volumes, (3) BET surface area (4) Total pore volume, (5) Morphology of crystallites constituting the ceramic microstructure, such as platelets or fibers, and (6) Purity of the support expressed either as total purity or surface purity.

However, in order to properly characterize porous bodies for applications in filters, membranes, or catalyst carriers, in addition to the above parameters it is also necessary to determine pore architecture and consequently fluid transport-related properties.

Among very important parameters in determining the diffusive gas transport through a porous body are tortuosity and constriction. Tortuosity is determined by the ratio of the real length of flow path through a porous body to the shortest distance across that porous body [see, for example, B. Ghanbarian et al., Soil Sci. Soc. Am. J., 77, 1461-1477 (2013)]. Constriction is a function of the area ratio of large pores to small pores. Thus, lowering the values of tortuosity and/or constriction enhances the diffusive transport through a porous material, i.e., increases the effective diffusivity, which is very important for instance in catalytic applications.

If there is a pressure drop across the porous body, permeability becomes important. Permeability indicates ability of fluids to flow through porous bodies and can be described by the Darcy's law shown in Equation 1, where V is fluid flow velocity, k is permeability, μ is dynamic viscosity of the fluid, ΔP is pressure difference across porous body with thickness of Δx:

$$V = \frac{k}{\mu} \frac{\Delta P}{\Delta x} \quad \text{(Eq. 1)}$$

Thus higher values of permeability will enhance the pressure-driven fluid flow across a porous body, which is important in such applications as sorption, filtration, or catalysis.

Surprisingly, the aforementioned fluid transport-determining properties of porous bodies cannot be found in the literature to characterize porous architectures, particularly as-related to catalyst carriers for epoxidation of olefins. Moreover, there has been no indication in the literature of the necessary values of tortuosity, constriction or permeability which provide a pore architecture to a porous body that can achieve enhanced properties, especially in regard to catalyst performance. The present invention provides porous bodies that have a pore architecture that has enhanced fluid transport properties, in particular effective gas diffusivity, and high mechanical integrity.

Unless otherwise specified the following methodology of measurements were employed in the present application.

Cumulative intrusion curves and Log differential intrusion curves were acquired for representative samples of the porous bodies by mercury (Hg) intrusion porosimetry, principles of which are described in Lowell et al., *Characterization of Porous Solids and Powders: Surface Area, Pore Size and Density*, Springer, 2006. The equipment used was AutoPore IV 9500 Series porosimeter from Micromeritics Instruments Co., Norcross, Ga. The Hg intrusion pressure ranged between 1.5 and 60,000 psi, which corresponds to pore sizes between 140 microns and 3.6 nm. The following Hg parameters were used for calculations: surface tension of 480 dynes/cm, density of 13.53 g/mL, and contact angle of 140°.

Pore volumes for the porous bodies were measured from the Hg intrusion data, which were consistent with the water absorption measurements.

In the present invention, water absorption of the porous bodies was measured by placing a 10 g representative sample of a porous body into a flask, which was then evacuated to about 0.1 torr for 5 min. Subsequently, deionized water was aspirated into the evacuated flask to cover the porous bodies while maintaining the pressure at about 0.1 torr. The vacuum was released after about 5 minutes to restore ambient pressure, hastening complete penetration of water into the pores. Subsequently, the excess water was drained from the impregnated sample. Water absorption was calculated by dividing total water weight in the pores (i.e., wet mass–dry mass of the sample) by the weight of the dry sample at room temperature.

Additional pore architecture parameters of the porous bodies such as tortuosity, constriction, and permeability, were also calculated from the Hg intrusion data, as described below.

The tortuosity, $\xi$ was calculated from Equation 2, where $D_{avg}$ is weighted average pore size, k is permeability, $\rho$ is true materials density, and $I_{tot}$ is total specific intrusion volume [See, *AutoPore V Operator Manual*, Micromeritics, 2014]:

$$\xi = \sqrt{\frac{D_{avg}^2}{4 \cdot 24k(1 - \rho I_{tot})}} \qquad (\text{Eq. 2})$$

The constriction, $\sigma$, was calculated from Equation 3, where $\xi$ is tortuosity and $\tau$ is tortuosity factor, calculated from the Carnigilia equation [See, *AutoPore V Operator Manual*, Micromeritics, 2014]:

$$\sigma = \frac{\xi}{\tau} \qquad (\text{Eq. 3})$$

The permeability, as defined by the Darcy's law (Eq. 1, above), can be calculated by combining Darcy's and Poiseuille'd equations [See, for example, Lowell et al., *Characterization of Porous Solids and Powders*, Springer, 2006]. For an arbitrary pore shape factor, f, the permeability k is expressed by Equation 4, where $\tau$ is tortuosity factor, P is materials porosity, and d is pore diameter:

$$k = \frac{P^3 d^2}{16 f \tau (1-P)^2} \qquad (\text{Eq. 4})$$

Once tortuosity and pore volumes have been measured, effective diffusivity can be calculated from Equation 5, where P is materials porosity, D is diffusivity, $D_{eff}$ is effective diffusivity, and $\xi$ is tortuosity [D. W. Green, R. H. Perry, *Perry's Engineering Handbook*, 8$^{th}$ Edition, McGraw-Hill, 2007]

$$D_{eff} = \frac{PD}{\xi} \qquad (\text{Eq. 5})$$

In order to calculate absolute values of effective diffusivity, $D_{eff}$, in a porous solid, absolute values of gas diffusivity, D, must be known per Eq. 5, in addition to the material porosity and tortuosity. However, in order to compare effective diffusivity properties of different porous solids (e.g., inventive examples of the present invention), it is possible to calculate relative numbers of effective diffusivity normalized to a standard material (comparative example of the present invention). With the assumption that gas diffusivity, D, is the same in all cases, it requires only knowledge of porosity and tortuosity of the porous materials (see Equation 6).

$$\frac{D_{eff,1}}{D_{eff,0}} = \frac{P_1}{\xi_1} \frac{\xi_0}{P_0} \qquad (\text{Eq. 6})$$

Total porosity is defined as the void volume divided by the total volume of the sample. It can be calculated from mercury porosimetry or water absorption, using theoretical density of the carrier material.

Specific surface areas of the porous bodies were determined by nitrogen adsorption using the B.E.T. method, details of which are described in Brunauer, S., Emmett, P. H. and Teller, *J. Am. Chem. Soc.*, 60, 309-16 (1938).

The flat plate crush strength of the porous bodies was measured using a standard test method for single pellet crush strength of formed catalysts and catalyst carriers, ASTM Standard ASTM D4179.

Attrition measurements of the porous bodies were performed using a standard test method for attrition and abrasion of catalysts and catalyst carriers, ASTM Standard ASTM D4058.

Scanning electron microscopy (SEM) was used to characterize pore architectures of the porous bodies of the present invention. The SEM photographs were acquired using Zeiss Auriga small Dual-Beam FIB-SEM. Pellets of each porous body were investigated on the cross-section (fracture surface) at 1.33 kV with about 5 mm working distance. No conductive coatings were sputtered on the samples.

As stated above, the present invention provides a porous body that has a pore architecture that has enhanced fluid transport properties and high mechanical integrity. The porous body of the present invention may be referred to as a porous ceramic body since it contains mainly alpha alumina particles. Typically, the porous body of the present invention comprises at least 80 percent alpha alumina; the remainder being other oxides and/or non oxides and incidental impurities. More typically, the porous body of the present invention comprises from 85 percent alpha alumina to 99 percent alpha alumina, the remainder being other oxides and/or non oxides and incidental impurities.

The porous body of the present invention typically has a pore volume from 0.3 mL/g to 1.2 mL/g. More typically, the porous body of the present invention has a pore volume from 0.35 mL/g to 0.9 mL/g. In some embodiments of the present invention, the porous body of the present invention has a water absorption from 30 percent to 120 percent, with a range from 35 percent to 90 percent being more typical.

The porous body of the present invention typically has a surface area from 0.3 m$^2$/g to 3.0 m$^2$/g. In one embodiment, the porous body of the present invention has a surface area from 0.5 m$^2$/g to 1.2 m$^2$/g. In another embodiment body of the present invention has a surface area above 1.2 m$^2$/g up to, and including, 3.0 m$^2$/g.

The porous body of the present invention can be monomodal or multimodal such as, for example, bimodal. The porous body of the present invention has a pore size distribution with at least one mode of pores in the range from 0.01 micrometers to 100 micrometers. In one embodiment of the present invention, at least 90 percent of the pore volume of the porous body is attributed to pores having a pore size of 20 microns or less. In yet another embodiment of the present invention, at least 85 percent of the pore volume of the porous body is attributed to pores having a size from 1 micron to 6 microns. In yet a further embodiment of the present invention, less than 15, preferably less than 10, percent of the pore volume of the porous body is attributed to pores having a size of less than 1 micron. In still a further embodiment of the present invention, at least 80 percent of the pore volume of the porous body is attributed to pores having a size from 1 micron to 10 microns. In a particular aspect of the present invention, there are essentially no pores smaller than 1 micron.

In one embodiment, the porous body of the present invention may be bimodal having a first set of pores from 0.01 microns to 1 micron and a second set of pores from greater than 1 micron to 10 microns. In such an embodiment, the first set of pores may constitute less than 15 percent of the total pore volume of the porous body, while the second set of pores may constitute more than 85 percent of the total pore volume of the porous body. In yet another embodiment, the first set of pores may constitute less than 10 percent of the total pore volume of the porous body, while the second set of pores may constitute more than 90 percent of the total pore volume of the porous body.

The porous body of the present invention typically has a total porosity that is from 55 percent to 83 percent. More typically, the porous body of the present invention has a total porosity that is from 58 percent to 78 percent.

The porous body of the present invention typically has an average flat plate crush strength from 10 N to 150 N. More typically, the porous body of the present invention has an average flat plate crush strength from 40 N to 105 N. In some embodiments, the porous body of the present invention can have an attrition value that is less than 40%, preferably less than 25%. In some embodiments of the present invention, the porous body can have attrition less that 10%.

In some embodiments of the present invention, the porous body has an initial low alkali metal content. By "low alkali metal content" it is meant that the porous body contains from 2000 ppm or less, typically from 30 ppm to 300 ppm, of alkali metal therein. Porous bodies containing low alkali metal content can be obtained by adding substantially no alkali metal during the porous body manufacturing process. By "substantially no alkali metal" it is meant that only trace amounts of alkali metal are used during the porous body manufacture process as impurities from other constituents of the porous body. In another embodiment, a porous body having a low alkali metal content can be obtained by performing various washing steps to the porous body precursor materials used in forming the porous body. The washing steps can include washing in a base, an acid, water, or another solvent.

In other embodiments of the present invention, the porous body has an alkali metal content that is above the value mentioned above for the porous body having substantially no alkali metal content. In such an embodiment the porous body typically contains a measurable level of sodium on the surface thereof. The concentration of sodium at the surface of the carrier will vary depending on the level of sodium within the different components of the porous body as well as the details of its calcination. In one embodiment of the present invention, the porous body has a surface sodium content of from 2 ppm to 150 ppm, relative to the total mass of the porous body. In another embodiment of the present invention, the porous body has a surface sodium content of from 5 ppm to 70 ppm, relative to the total mass of the carrier. The sodium content mentioned above represents that which is found at the surface of the carrier and that which can be leached, i.e., removed, by nitric acid (hereafter referred to as acid-leachable sodium).

The quantity of acid leachable sodium present in the porous bodies of the present invention can be extracted from the catalyst or carrier with 10% nitric acid in deionized water at 100° C. The extraction method involves extracting a 10-gram sample of the catalyst or carrier by boiling it with a 100 ml portion of 10% w nitric acid for 30 minutes (1 atm., i.e., 101.3 kPa) and determining in the combined extracts the relevant metals by using a known method, for example atomic absorption spectroscopy (See, for example, U.S. Pat. No. 5,801,259 and U.S. Patent Application Publication No. 2014/0100379 A1).

In one embodiment of the present invention, the porous body may have a silica content, as measured as $SiO_2$, of less than 0.2, preferably less than 0.1, weight percent, and a sodium content, as measured as $Na_2O$, of less than 0.2 weight percent, preferably less than 0.1, weight percent. In some embodiments, the porous body of the present invention may have an acid leachable sodium content of 40 ppm or less. In yet further embodiments of the present invention, the porous body comprises alumina crystallites having a platelet morphology in a content of less than 20 percent by volume. In some embodiments, alumina crystallites having a platelet morphology in a content of less than 10 percent by volume are present in the porous body of the present invention.

In addition to the above physical properties, the porous body of the present invention has a pore architecture that provides at least one of a tortuosity of 7 or less, a constriction of 4 or less and a permeability of 30 mdarcys or greater. A porous body that has the aforementioned pore architecture has enhanced fluid transport properties and high mechanical integrity. In some embodiments, and when used as a carrier for a silver-based epoxidation catalyst, a porous body having the aforementioned pore architecture can exhibit improved catalyst properties. Typically, the pore architecture of the porous body of the present invention has a tortuosity of 7 or less and/or a constriction of 4 or less.

In one embodiment of the present invention, the porous body has a pore architecture that provides a tortuosity of 7 or less. In another embodiment, the porous body of the present invention has a pore architecture that provides a tortuosity of 6 or less. In yet another embodiment, the porous body of the present invention has a pore architecture that provides a tortuosity of 5 or less. In a further embodiment, the porous body of the present invention has a pore architecture that provides a tortuosity of 3 or less. The lower limit of the tortuosity of the porous body of the present invention is 1 (theoretical limit). In some embodiments, the tortuosity can be any number bounded between 1 and 7.

In one embodiment of the present invention, the porous body has a pore architecture that provides a constriction of 4 or less. In another embodiment, the porous body of the present invention has a pore architecture that provides a constriction of 3 or less, or even 2 or less. The lower limit of the constriction of the porous body of the present invention is 1. In some embodiments, the constriction can be any number bounded between 1 and 4.

In yet another embodiment of the present invention, the porous body has 2-4 times improved effective gas diffusivity due to the combination of low tortuosity and high porosity.

In one embodiment, the porous body of the present invention has a pore architecture that provides a permeability of 30 mdarcys or greater. In another embodiment, the porous body of the present invention has a pore architecture that provides a permeability of 200 mdarcys or greater.

The porous bodies of the present invention can be prepared by first providing a precursor mixture comprising alpha alumina powders, non-silicate binder, burn-out materials, solvents, and lubricants. An example of a non-silicate binder is boehmite (γ-AlOOH). Typically, the non-silicate binder is dispersed into deionized water or another solvent. In the present invention, the alpha alumina powder that is used in the precursor mixture is a milled alpha alumina powder that has a particle size from 0.1 microns to 6 microns. All components of the porous body precursor mixture are homogenously mixed.

The principle burnout material that can be used in the present invention comprises any conventional burnout material having a particle size from 1 micron to 10 microns. Some examples of burnout materials that can be used as the principle burnout material include cellulose, substituted celluloses, e.g., methylcellulose, ethylcellulose, and carboxyethylcellulose, stearates (e.g., organic stearate esters, such as methyl or ethyl stearate), waxes, granulated polyolefins (e.g., polyethylene and polypropylene), walnut shell flour, and the like, which are decomposable at the firing temperatures used in preparation of the porous body. In one example, polyethylene having a particle size from 3 microns to 8 microns can be used as the principle burnout material. In another example, paraffin or PTFE having a particle size from 1 micron to 9 microns can be used as the principal burnout material.

In some embodiments, unmilled alpha alumina powder may be added to the precursor mixture. In other embodiments, the unmilled alpha alumina powder can be added to the precursor mixture mentioned above together with the milled alpha alumina powder. The unmilled alpha alumina powder that can be used in the present invention may have an average particle size in a range from 10 microns to 100 microns. When unmilled alpha alumina powder is employed, the weight ratio of milled alpha alumina powder to unmilled alpha alumina powder can be from about 0.25:1 to about 5:1.

An auxiliary burnout material can be optionally added to the precursor mixture. When employed, the auxiliary burnout material has a particle size that is greater than the particle size of the principle burnout material mentioned above. The auxiliary burnout material may be a same, or different, burnout material as the principle burnout material. In one example, graphite having a particle size from 3 microns to 10 microns can be used as the auxiliary burnout material. In another example, paraffin or PTFE having a particle size from 1 micron to 9 microns can be used as the auxiliary burnout material. When an auxiliary burnout material is used, the weight ratio of the principal burnout material to the auxiliary burnout material can be in a range from 1.1 to 5.4.

In the precursor mixture mentioned above, a conventional lubricant such as, for example, Petrolatum, can be used. The amount of lubricate that can be added at this point of the present invention may comprise the total amount of, or a partial amount, of the lubricate that used in forming the porous bodies of the present invention.

In some embodiments of the present invention, additional unmilled alpha alumina powder having a larger particle size than the previously mentioned unmilled alpha alumina powder may be added to the precursor mixture. When the additional unmilled alpha alumina powder is employed, the weight ratio of milled alpha alumina powder to additional unmilled alpha alumina powder can be from about 0.2:1 to about 5:1. In some embodiments, additional lubricate can be added to the precursor mixture.

The precursor mixture mentioned above is then formed to provide a desired shape of the porous body. The shape may vary and can be selected based upon the desired application of the resultant porous body that is eventually formed. Forming of the precursor mixture is typically performed by pressing, extrusion, molding, casting, etc. In one embodiment of the present invention, extruding may be performed using an extruder die that can produce hollow cylinder shapes which then can be cut to pieces of substantially equal length. The extrudate after cutting is then dried using any conventional drying means. Subsequently, the dried extrudate can be transferred into a furnace in order to remove the water and burn out most of the burnout materials and other fillers that may be present. Depending on the burnout material type, heat treatment can performed at temperatures from 100° C. to 1,000° C. with heating rates varying between 10° C./hr to 100° C./hr. Subsequently, the extrudate can be sintered. In one example, sintering may be performed in flowing air at a temperature from 1200° C. to 1600° C. After sintering, the resultant porous body is cooled to room temperature. The heating and cooling rates can be within a range from 1° C./min up to 5° C./min. Other heating and cooling rates within a range from 0.5° C./min up to 20° C./min can also be used in the present invention for providing the porous bodies.

In one embodiment, the porous body contains essentially only alumina, or alumina and boehmite components, in the absence of other metals or chemical compounds except that trace quantities of other metals or compounds may be present. A trace amount is an amount low enough that the trace species does not observably affect functioning or ability of a catalyst prepared thereupon.

In one embodiment of the present invention, the porous body described above can be used as a catalyst carrier (i.e., catalyst support) which includes one or more catalytically active materials, typically metals, disposed on and/or in the porous body. The one or more catalytically active materials can catalyze a specific reaction and are well known in the art. In some embodiments, the catalytically active material includes one or more transition metals from Groups 3-14 of the Periodic Table of Elements and/or Lanthanides. In such applications, one or more promoting species (i.e., species that aide in a specific reaction) can be also disposed on and/or in the porous body of the present invention. The one or more promoting species may be, for example, alkali metals, alkaline earth metals, transition metals, and/or an element from Groups 15-17 of the Periodic Table of Elements.

In another embodiment of the present invention, the porous body described above can also be used as a filter in which liquid or gas molecules can diffuse through the pores of the porous body described above. In such an application, the porous body can be placed along any portion of a liquid or gas stream flow. In yet another embodiment of the present invention, the porous body described above can be used as a membrane.

The porous body of the present application can be particularly useful as a carrier for a silver-based epoxidation catalyst. In such an embodiment, a catalytically effective amount of silver is disposed on and/or in the porous body.

In one embodiment, the catalytic amount of silver is from 10% by weight to 50% by weight. The catalytic amount of silver may be achieved utilizing a single impregnation or multiple impregnations may be used, as described below, and calcinations, as also defined below.

The silver-based epoxidation catalyst can be prepared by impregnating the porous body described above with silver ions, compounds, complexes, and/or salts dissolved in a suitable solvent sufficient to cause deposition of silver precursor compound onto and/or into the porous body. In some embodiments of the present invention, and as will be described in greater detail herein below, the porous body described above can be simultaneously impregnated and incorporated with silver along with any additional desired promoter or additional promoter combination, by any of the conventional methods known in the art, e.g., by excess solution impregnation, incipient wetness impregnation, spray coating, and the like. Typically, the porous body described above is placed in contact with the silver-containing solution until a sufficient amount of the solution is absorbed by the porous body. Infusion of the silver-containing solution into the porous body can be aided by invention of a vacuum. A single impregnation or a series of impregnations, with or without intermediate drying, may be used, depending in part on the concentration of the silver component in the solution. Impregnation procedures are described in, for example, U.S. Pat. Nos. 4,761,394, 4,766,105, 4,908,343, 5,057,481, 5,187,140, 5,102,848, 5,011,807, 5,099,041 and 5,407,888, all of which are incorporated herein by reference. Known procedures for pre-deposition, co-deposition, and post-deposition of the various promoters can also be employed.

Silver compounds useful for catalyst deposition by impregnation include, for example, silver oxalate, silver nitrate, silver oxide, silver carbonate, a silver carboxylate, silver citrate, silver phthalate, silver lactate, silver propionate, silver butyrate and higher fatty acid salts and combinations thereof. The silver solution used to impregnate the carrier can contain any suitable solvent. The solvent can be, for example, water-based, organic-based, or a combination thereof. The solvent can have any suitable degree of polarity, including highly polar, moderately polar or non-polar, or substantially or completely non-polar. The solvent typically has sufficient solvating power to solubilize the solution components. A wide variety of complexing or solubilizing agents may be employed to solubilize silver to the desired concentration in the impregnating medium. Useful complexing or solubilizing agents include amines, ammonia, lactic acid and combinations thereof. For example, the amine can be an alkylene diamine having from 1 to 5 carbon atoms. In one embodiment, the solution comprises an aqueous solution of silver oxalate and ethylene diamine. The complexing/solubilizing agent may be present in the impregnating solution in an amount from about 0.1 moles to about 10 moles of ethylene diamine per mole of silver, preferably from about 0.5 moles to about 5 moles, and more preferably from about 1 moles to about 4 moles of ethylene diamine for each mole of silver.

The concentration of silver salt in the solution is typically in the range from about 0.1% by weight to the maximum permitted by the solubility of the particular silver salt in the solubilizing agent employed. More typically, the concentration of silver salt is from about 0.5% by weight of silver to 45% by weight of silver, and even more typically, from about 5% by weight of silver to 35% by weight of silver.

In addition to silver, the silver-based epoxidation catalyst of the present invention may also include any one or more promoting species in a promoting amount. The one or more promoting species can be incorporated into the porous body described above either prior to, coincidentally with, or subsequent to the deposition of the silver. As used herein, a "promoting amount" of a certain component refers to an amount of that component that works effectively to provide an improvement in one or more of the catalytic properties of a subsequently formed catalyst when compared to a catalyst not containing the component.

For example, silver-based epoxidation catalysts may include a promoting amount of a Group 1 alkali metal or a mixture of two or more Group 1 alkali metals. Suitable Group 1 alkali metal promoters include, for example, lithium, sodium, potassium, cesium, rubidium, or combinations thereof. Thus, and in one example, a silver-based epoxidation catalyst including silver and one of lithium, sodium, potassium, cesium and rubidium can be provided in the present invention. The amount of alkali metal will typically range from about 10 ppm to about 3000 ppm, more typically from about 15 ppm to about 2000 ppm, more typically from about 20 ppm to about 1500 ppm, and even more typically from about 50 ppm to about 1000 ppm by weight of the total catalyst, expressed in terms of the additional alkali metal.

The silver-based epoxidation catalyst may also include a promoting amount of a Group 2 alkaline earth metal or a mixture of two or more Group 2 alkaline earth metals. Suitable alkaline earth metal promoters include, for example, beryllium, magnesium, calcium, strontium, and barium or combinations thereof. The amounts of alkaline earth metal promoters are used in similar amounts as the alkali metal promoters described above.

The silver-based epoxidation catalyst may also include a promoting amount of a main group element or a mixture of two or more main group elements. Suitable main group elements include any of the elements in Groups 13 (boron group) to 17 (halogen group) of the Periodic Table of the Elements. In one example, a promoting amount of one or more sulfur compounds, one or more phosphorus compounds, one or more boron compounds or combinations thereof can be used.

The silver-based epoxidation catalyst may also include a promoting amount of a transition metal or a mixture of two or more transition metals. Suitable transition metals can include, for example, the elements from Groups 3 (scandium group), 4 (titanium group), 5 (vanadium group), 6 (chromium group), 7 (manganese group), 8-10 (iron, cobalt, nickel groups), and 11 (copper group) of the Periodic Table of the Elements, as well as combinations thereof. More typically, the transition metal is an early transition metal selected from Groups 3, 4, 5, 6, or 7 of the Periodic Table of Elements, such as, for example, hafnium, yttrium, molybdenum, tungsten, rhenium, chromium, titanium, zirconium, vanadium, tantalum, niobium, or a combination thereof.

In one embodiment of the present invention, the silver-based epoxidation catalyst includes silver, cesium, and rhenium. In another embodiment of the present invention, the silver-based epoxidation catalyst includes silver, cesium, rhenium and one or more species selected from Li, K, W, Zn, Mo, Mn, and S.

The silver-based epoxidation catalyst may also include a promoting amount of a rare earth metal or a mixture of two or more rare earth metals. The rare earth metals include any of the elements having an atomic number of 57-71, yttrium (Y) and scandium (Sc). Some examples of these elements include lanthanum (La), cerium (Ce), and samarium (Sm).

The transition metal or rare earth metal promoters are typically present in the silver-based epoxidation catalyst in an amount of from about 0.1 micromoles per gram to about 10 micromoles per gram, more typically from about 0.2 micromoles per gram to about 5 micromoles per gram, and even more typically from about 0.5 micromoles per gram to about 4 micromoles per gram of total catalyst, expressed in terms of the metal.

All of the aforementioned promoters, aside from the alkali metals, can be in any suitable form, including, for example, as zerovalent metals or higher valent metal ions.

After impregnation with silver, and any promoters, the impregnated porous alumina body is removed from the solution and calcined for a time sufficient to reduce the silver component to metallic silver and to remove volatile decomposition products from the silver-containing porous alumina body. The calcination is typically accomplished by heating the impregnated porous alumina body, preferably at a gradual rate, to a temperature in a range of about 200° C. to about 600° C., more typically from about 200° C. to about 500° C., more typically from about 250° C. to about 500° C., and more typically from about 200° C. or 300° C. to about 450° C., at a reaction pressure in a range from about 0.5 to about 35 bar. In general, the higher the temperature, the shorter the required calcination period. A wide range of heating periods have been described in the art for the thermal treatment of impregnated carriers. See, for example, U.S. Pat. No. 3,563,914, which indicates heating for less than 300 seconds, and U.S. Pat. No. 3,702,259, which discloses heating from 2 to 8 hours at a temperature of from 100° C. to 375° C. to reduce the silver salt in the catalyst. A continuous or step-wise heating program may be used for this purpose. During calcination, the impregnated porous alumina body carrier is typically exposed to a gas atmosphere comprising oxygen, such as air, or an inert gas, such as nitrogen, or both. The inert gas may also include a reducing agent as well known in the art.

The silver-based epoxidation catalyst mentioned above can be used in a method for the vapor phase production of ethylene oxide by conversion of ethylene to ethylene oxide in the presence of oxygen. With the exception of during the initiation phase of the invention which is the subject of this invention and is described in greater detailed below, the ethylene oxide production process is conducted by continuously contacting an oxygen-containing gas with ethylene in the presence of the above described silver-based epoxidation catalyst at a temperature in the range from about 180° C. to about 330° C., more typically from about 200° C. to about 325° C., and more typically from about 225° C. to about 280° C., at a pressure which may vary from about atmospheric pressure to about 30 atmospheres depending on the mass velocity and productivity desired. While the above temperature ranges are acceptable, typically 280° C. is about the highest temperature at which most EO plants can operate and is about the highest temperature at which the catalyst can effectively perform. Above 280° C. there is significant sintering and migration of silver and active sites as previously mentioned, effectively destroying catalyst performance. Typical process for the oxidation of ethylene to ethylene oxide comprises the vapor phase oxidation of ethylene with molecular oxygen in the presence of the catalyst of the present invention in a fixed bed, tubular reactor. Conventional commercial fixed bed ethylene oxide reactors are typically in the form of a plurality of parallel elongated tubes (in a suitable shell). In one embodiment, the tubes are approximately 0.7 to 2.7 inches O.D. and 0.5 to 2.5 inches I.D. and 15-45 feet long filled with the silver-based epoxidation catalyst described above.

The silver-based epoxidation catalyst described above has been shown to be a particularly selective catalyst in the oxidation of ethylene with molecular oxygen to ethylene oxide. Selectivity values of at least about 83 mol % up to about 93 mol % are typically achieved. In some embodiments, the selectivity is from about 87 mol % to about 93 mole %. The conditions for carrying out such an oxidation reaction in the presence of the silver-based epoxidation catalyst described above broadly comprise those described in the prior art. This applies, for example, to suitable temperatures, pressures, residence times, reactor feed components (e.g., nitrogen, carbon dioxide, steam, argon, and methane), the presence or absence of moderating agents to control the catalytic action (e.g., 1,2-dichloroethane, vinyl chloride or ethyl chloride), the desirability of employing recycle operations or applying successive conversion in different reactors to increase the yields of ethylene oxide, and any other special conditions which may be selected in processes for preparing ethylene oxide.

In the production of ethylene oxide, after the initiation phase of the invention described below, when the catalyst has lined-out and full production levels are reached, the reactant feed mixture typically contains from about 0.5 to about 45% ethylene and from about 3 to about 15% oxygen, with the balance comprising comparatively inert materials including such substances as nitrogen, carbon dioxide, methane, ethane, argon and the like. Only a portion of the ethylene is typically reacted per pass over the catalyst. After separation of the desired ethylene oxide product and removal of an appropriate purge stream and carbon dioxide to prevent uncontrolled build up of inert products and/or by-products, unreacted materials are typically returned to the oxidation reactor.

In other embodiments, the process of ethylene oxide production includes the addition of oxidizing gases to the feed to increase the efficiency of the process. For example, U.S. Pat. No. 5,112,795 discloses the addition of 5 ppm of nitric oxide to a gas feed having the following general composition: 8 volume % oxygen, 30 volume % ethylene, about 5 ppmw ethyl chloride, and the balance nitrogen.

The resulting ethylene oxide that is produced can be separated and recovered from the reaction products using methods known in the art. The ethylene oxide process may include a gas recycle process wherein a portion or substantially all of the reactor effluent is readmitted to the reactor inlet after substantially removing the ethylene oxide product and byproducts. In the recycle mode, carbon dioxide concentrations in the gas inlet to the reactor may be, for example, from about 0.3 to about 6, preferably from about 0.3 to about 2.0, volume percent.

The full production stage of catalyst operation described above is preceded by an initiation phase. The initiation phase starts with the fresh, unused catalyst and proceeds by reacting a feed gas composition containing ethylene, oxygen, carbon dioxide, chlorides and other feed gas components in the presence of the silver-based epoxidation catalyst at a temperature of about 200° C. to about 230° C. As mentioned above, an important aspect of the present invention is contrary to the prior art, the temperature during initiation is much lower. Another important aspect of the present invention it that reactor feed has a relatively high ethylene to oxygen ratio. Accordingly, the molar ratio of ethylene:oxygen in the feed is preferably from about 2.5:1 to about 12:1. Thus, preferably the feed contains about 20 mol % to about 35 mol % ethylene and about 3 mol % to 8 mol % oxygen. As also discussed above the present invention does not require high concentration of carbon dioxide so that preferably the feed gas contains less than 2 mol % carbon dioxide. After initiation at an initial temperature of about 200° C. to about 230° C. the temperature is subsequently increased either stepwise or continuously. If stepwise, the temperature is increased to one or more higher temperatures above the initial temperature, with each separate temperature step or increase being about 5° C. to about 10° C. than the previous temperature step and with each temperature being held or maintained before being increased to the next temperature level for at least about 5 hours, preferably between about 10 hours to about 100 hours, more preferably between about 20 hours to about 75 hours. As an example of this stepwise process, after initiation at the initial temperature there is a stepwise temperature increase of about 5° C. to about 10° C. to a second temperature which is maintained for about 10 hours to about 100 hours and then subsequently a stepwise increase of about 5° C. to about 10° C. to a third temperature which is maintained for about 10 hours to about 100 hours.

the temperature may be subsequently increased to a second temperature about 5° C. to 10° C. than the initial temperature and held at the second temperature for about 25 hours to about 100 hours and then subsequently there is a stepwise increase to a third temperature again about 5° C. to 10° C. than the initial temperature and held at the third temperature for about 25 hours to about 100 hours. The catalyst is then ready to operate at normal production levels.

An especial advantage of the present invention is that unlike in prior art process, in the present invention the initiation phase is operated at temperature levels and reactor feed compositions (e.g., ethylene, oxygen, and carbon dioxide levels) that are normal and typical for full production in an ethylene oxide plant. Unlike in prior art processes where an adjustment phase is necessary to lower temperatures from highly elevated levels and to adjust feed gas compositions containing high CO2 and relatively low ethylene to oxygen ratios, in the present invention the initiation phase leads naturally into "lined-out" levels at normal EO process production values. Thus, in the present invention the temperature is continually increased as described above until ethylene oxide production levels comparable to full production levels are reached, during which the ΔEO is greater than about 1.5%, preferably greater than about 2.5%, more preferably in the range of 2.0% to 4.0%.

Examples have been set forth below for the purpose of further illustrating the present invention. The scope of the present invention is not limited to the examples set forth herein. Other examples, such as porous filters, membranes, and other types of catalysts, are not discussed in more detail.

EXAMPLE

The invention will now be described in more detail with respect to the following example.

Two identical catalysts samples were prepared as described herein and according to the present invention. These catalyst samples were then crushed, ground and screened to provide a sample of 14-18 mesh particles. 9.0 grams of the material were then charged into two separate ¼" outer diameter heated microreactors with automated chloride control at a ΔEO of 3.8 mol %, and at a work rate of 355 kg EO/m³ cat/h. The process in the first microreactor was operated according to the present invention with the catalyst being conditioned or initiated at a relatively low temperature of 220° C., which is then gradually increased in a stepwise pattern as shown in the temperature profile set forth in FIG. 1. The feed composition in the first microreactor, was: 30% ethylene, 7% oxygen, 1% carbon dioxide and the balance nitrogen while maintaining chloride levels between 0.5 and 6 ppm. Thus, according to the present invention there was a relatively high ethylene to oxygen ratio in the feed gas.

Figure 1:
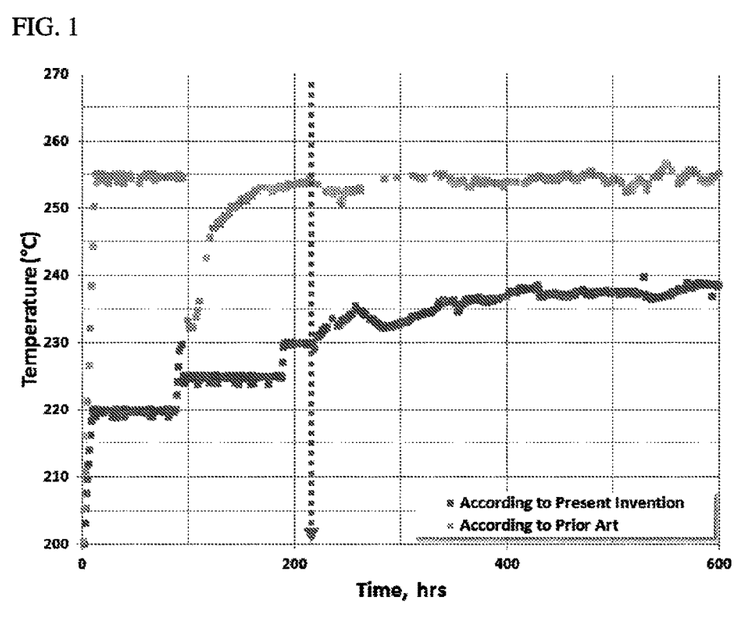
FIG. 1 is a graph for an ethylene oxide catalyst and process plotting the activity versus time for operation according to the prior art and according to the present invention.

By contrast, the process in the second microreactor was operated according to the prior art with the catalyst being conditioned or initiated under a relatively low ethylene to oxygen ratio atmosphere of 8% ethylene, 4% oxygen, 4% carbon dioxide, and 1 ppm chlorides at a temperature of 255° C. for 100 hours after which the feed composition to the second microreactor was changed to 30% ethylene, 7% oxygen, 1% carbon dioxide, and 1 ppm chlorides; with the temperature being lowered at the completion of initiation as shown in FIG. 1.

Figure 2:
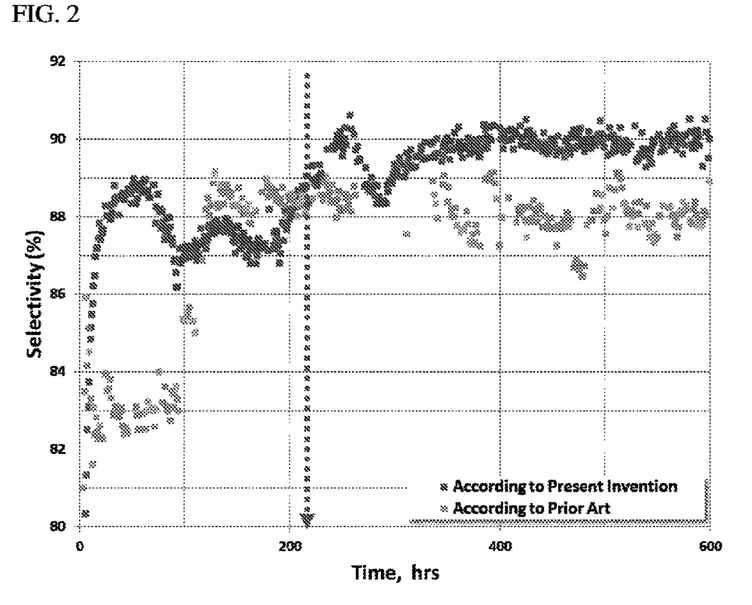
FIG. 2 is a graph for an ethylene oxide catalyst and process plotting selectivity versus time for operation according to the prior art and according to the present invention.

As can be seen in both FIG. 1 and FIG. 2, the performance of the catalyst operated according to the present invention is superior both in being more active and having a significantly higher selectivity. While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. A method of improving the performance of a silver-based epoxidation catalyst comprising a carrier comprising at least 80 percent alpha alumina and having a pore volume from 0.3 mL/g to 1.2 mL/g, a surface area from 0.3 m²/g to 3.0 m²/g, and a pore architecture that provides at least one of a tortuosity of 7 or less, a constriction of 4 or less and a permeability of 30 mdarcys or greater; a catalytic amount of silver disposed on and/or in said carrier; and a promoting amount of one or more promoters disposed on said carrier; which method further comprises:

initiating an epoxidation reaction by reacting a feed gas composition containing ethylene and oxygen present in a ratio of from about 2.5:1 to about 12:1, in the presence of the silver-based epoxidation catalyst at a temperature of about 200° C. to about 230° C.; and
   subsequently increasing the temperature either stepwise or continuously.

2. The method according to claim 1, wherein the subsequently increasing step is conducted stepwise.

3. The method according to claim 2, wherein each temperature step is held for a period of about 20 hours to about 100 hours.

4. The method according to claim 1, wherein the feed gas composition contains about 20 mol % to about 35 mol % ethylene, about 3 mol % to 8 mol % oxygen, and less than 2 mol % carbon dioxide.

5. The method according to claim 1, wherein said one or more promoters comprise Group 1 alkali metal promoters, one or more transition metals, one or more Group 2 alkaline earth metals or any combination thereof.

6. The method according to claim 1, wherein the subsequently increasing step comprises a stepwise temperature increase of about 5° C. to about 10° C. to a second temperature and maintained at the second temperature for about 25 hours to about 100 hours and then subsequently a stepwise increase of about 5° C. to about 10° C. to a third temperature and maintained at the third temperature for about 25 hours to about 100 hours.

7. The method according to claim 1, wherein the subsequently increasing step comprises increasing the temperature stepwise to one or more higher temperature steps with each temperature step being about 5° C. to about 10° C. than a previous temperature step.

8. The method according to claim 1, wherein said one or more transition metals comprise rhenium, molybdenum, tungsten, or any combination thereof.

9. The method according to claim 1, wherein said Group 1 alkali metal promoters are selected from the group consisting of cesium, lithium, sodium, potassium, and rubidium.

10. The method according to claim 1, wherein said one or more promoters comprises a promoting combination of rhenium, cesium and lithium.

11. The method according to claim 1, wherein said catalytic amount of silver is from 10 to 50% by weight.

12. The method according to claim 1, wherein said carrier has alumina crystallites having a platelet morphology in a content of less than 20 percent by volume.

\* \* \* \* \*